United States Patent
Vanderlaan et al.

(10) Patent No.: US 6,634,748 B1
(45) Date of Patent: Oct. 21, 2003

(54) METHODS OF STABILIZING SILICONE HYDROGELS AGAINST HYDROLYTIC DEGRADATION

(75) Inventors: Douglas G. Vanderlaan, Jacksonville, FL (US); Stephen L. Galas, Jacksonville, FL (US)

(73) Assignee: Johnson & Johnson Vision Care, Inc., Jacksonville, FL (US)

(*) Notice: Subject to any disclaimer, the term of this patent is extended or adjusted under 35 U.S.C. 154(b) by 280 days.

(21) Appl. No.: 09/713,464

(22) Filed: Nov. 15, 2000

(51) Int. Cl.[7] .................................................. G02C 7/02
(52) U.S. Cl. ................... 351/177; 351/160 H; 514/839; 514/970
(58) Field of Search .......................... 351/177, 160 R, 351/160 H; 623/6.11, 6.56; 514/839–840, 912, 915, 970, 975; 134/901; 422/28; 424/427, 429

(56) References Cited

U.S. PATENT DOCUMENTS

| | | |
|---|---|---|
| 5,618,492 A | 4/1997 | Auten et al. .................. 422/22 |
| 5,882,687 A | 3/1999 | Park et al. .................. 424/682 |
| 6,024,954 A * | 2/2000 | Park et al. .................. 424/94.2 |
| 6,281,192 B1 * | 8/2001 | Leahy et al. .................. 514/8 |
| 2002/0018732 A1 * | 2/2002 | Hung et al. .................. 422/28 |

FOREIGN PATENT DOCUMENTS

| | | |
|---|---|---|
| WO | WO 99 24541 A | 5/1999 |
| WO | WO 00 35500 A | 6/2000 |
| WO | WO 00 37048 A | 6/2000 |

OTHER PUBLICATIONS

PCT International Search Report, dated Oct. 16, 2002 for PCT Int'l. Appln. No. PCT/US01/48474.

* cited by examiner

Primary Examiner—Jordan M. Schwartz

(57) ABSTRACT

A method of increasing the shelf life of silicone hydrogels stored in aqueous solutions. More specifically, the present invention relates to a method of stabilizing a silicone hydrogel article against hydrolytic degradation comprising, storing said silicone hydrogel in an ozone-free, aqueous solution having a pH of from about 5.0 to less than about 7.2, and a viscosity of less than about 10 centipoise, wherein if the aqueous solution is substantially free of poloxamine or poloxamer surfactants.

10 Claims, 1 Drawing Sheet

Figure 1 - Effect of pH on Modulus

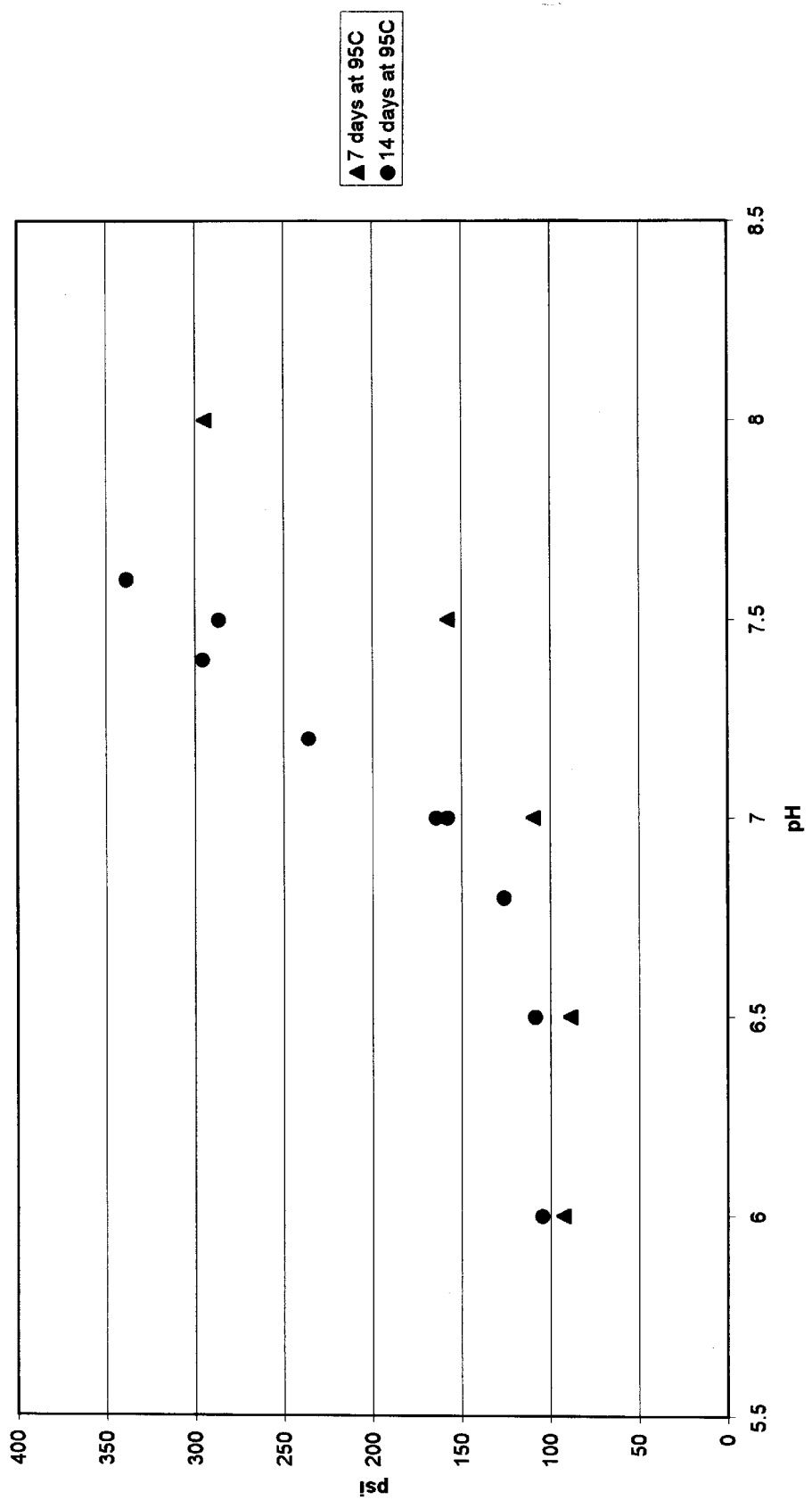

US 6,634,748 B1

METHODS OF STABILIZING SILICONE HYDROGELS AGAINST HYDROLYTIC DEGRADATION

FIELD OF THE INVENTION

This invention relates to methods of stabilizing silicone hydrogels against hydrolytic degradation.

BACKGROUND OF THE INVENTION

Contact lenses have been used commercially to improve vision since at least the 1950s. The first contact lenses were made of hard materials and as such were somewhat uncomfortable to users. Modern lenses have been developed that are made of softer materials, typically hydrogels and particularly silicone hydrogels. Hydrogels are water-swollen polymer networks that have high oxygen permeability and provide good comfort to lens users. These materials have enabled many more patients to wear lenses due to their increased comfort. Despite the advantages of these lenses to patients, the same lenses present unique problems to the manufactures of those lenses.

Contact lenses, like other medical devices, are stored in aqueous solutions. The mechanical properties of silicone hydrogel contact lenses degrade over time when lenses are stored at ambient or elevated temperature in aqueous solutions. This degradation, shortens the shelf life of a silicone hydrogel and can be quantified by measuring the increase in tensile modulus. Therefore, there is a need to find a method of increasing the stability of silicone hydrogel contact lenses in aqueous solutions. It is this need that this invention fills.

BRIEF DESCRIPTION OF THE DRAWINGS

FIG. 1 Graph illustrating the effect of pH on tensile modulus.

DETAILED DESCRIPTION OF THE INVENTION

This invention includes a method of stabilizing a silicone hydrogel article against hydrolytic degradation comprising, consisting essentially of, or consisting of, storing said silicone hydrogel in an ozone-free, aqueous solution having a pH of from about 5.0 to less than about 7.2, and a viscosity of less than about 10 centipoise, wherein if the aqueous solution contains a poloxamine or poloxamer surfactant, the surfactant is present in an amount less than about 0.005 weight percent.

As used herein, the term "silicone hydrogel article" refers polymers that absorb water and are made of at least one silicone monomer, co-polymerized with a hydrophilic monomer. Examples of typical silicone monomers include but are not limited to 3-methacryloxypropyl tris (trimethylsiloxy)silane (TRIS), and monomethacryloxypropyl terminated polydimethylsiloxane (mPDMS), m vinyl[3-[3,3,3-trimethyl-1,1bis(trimethylsiloxy)disiloxanyl]propyl] carbamate , 3-methacryloxypropylbis(trimethylsiloxy) methyl silane, and methacryloxypropylpentamethyl disiloxane. Additional monomers are described in U.S. Pat. Nos. 4,711,943; 3,808,178; 4,139,513; 5,070,215; 5,710, 302; 5,714,557; 5,908,906; 4,136,250; 4,153,641; 4,740, 533; 5,034,461; 5,070,215; 5,260,000; 5,310,779; and 5,358,995 which are hereby incorporated by reference for the silicone monomers contained therein. Examples of hydrophilic monomers include but are not limited to unsaturated carboxylic acids, such as methacrylic and acrylic acids; acrylic substituted alcohols, such as 2-hydroxyethylmethacrylate and 2-hydroxyethylacrylate; vinyl lactams, such as N-vinyl pyrrolidone; and acrylamides, such as methacrylamide and N,N-dimethylacrylamide. Still further examples include β-alanine-N-vinyl ester, the hydrophilic vinyl carbonate or vinyl carbamate monomers disclosed in U.S. Pat. No. 5,070,215, and the hydrophilic oxazolone monomers disclosed in U.S. Pat. No. 4,910,277. U.S. Pat. Nos. 5,070,215, and 4,910,277 are hereby incorporated by reference with respect to the silicone monomers contained therein.

This invention can be used in conjunction with all types of silicone hydrogels articles. The problem of modulus increase associated with hydrolytic degradation may be particularly pronounced when silicone hydrogels contain carboxylic acid-functional monomers. Silicone hydrogels containing those monomers suffer more hydrolytic degradation upon standing than those that do not contain monomers with carboxylic acid functionality.

Silicone hydrogels are used to form a number of medical devices, particularly contact lenses and intraocular lenses. Examples of procedures to prepare silicone hydrogel contact lenses may be found in U.S. Pat. No. 5,260,000, U.S. Pat. No. 6,037,328, U.S. Pat. No. 5,998,498, U.S. patent application Ser. No. 09/532,943, a continuation-in-part of U.S. patent application Ser. No. 09/532,943 filed on Aug. 30, 2000, U.S. Pat. No. 6,087,415, U.S. Pat. No. 5,962,548, and U.S. Pat. No. 6,020,445. This invention is particularly suited for contact lens made from acquafilcon A, balafilcon A and lotrafilcon.

"Ozone-free" solutions are those that do not contain dissolved ozone, other than the ozone that diffuses into the solution from the atmosphere. "Aqueous solutions" include but are not limited to any water based solution that is used for the storage or washing of contact lenses. Typical solutions include saline solutions, other buffered solutions, and deionized water. The preferred aqueous solution is a saline solution where the salts contained therein are selected from one or more members of the group consisting of sodium chloride, boric acid, sodium borate, sodium phosphate, sodium hydrogenphosphate, sodium dihydrogenphosphate, or the corresponding potassium salts of the same. These salts are generally combined to form buffered solutions which include an acid and its conjugate base, so that addition of acids and bases cause only a relatively small change in pH. The buffered solutions may additionally include 2-(N-morpholino)ethanesulfonic acid (MES), NaOH, 2,2-bis (hydroxymethyl)-2,2',2"-nitrilotriethanol, HCI, n-tris (hydroxymethyl)methyl-2-aminoethanesulfonic acid, citric acid, sodium citrate, sodium carbonate, sodium bicarbonate, acetic acid, sodium acetate. The concentration of salt in the aqueous solution is about 0.3 to 3.0 weight percent, preferably about 0.5 to 2.0 percent, more preferably about 0.6 to 1.3 percent. The preferred buffer solutions are borates and phosphates.

The pH of the aqueous solution can be adjusted to a pH of about of about 5.0 to less than about 7.2 by the addition of aqueous HCI or aqueous NaOH. The preferred pH ranges from about 6.0 to about less than 7.2, more preferably from about 6.8 to about 7.2, most preferably from about 6.8 to about 7.1. The viscosity of the aqueous solution is less than about 10 centipoise and preferably less than about 7 centipoise.

Further, the invention includes a hydrolytically stable silicone hydrogel contact lens that is produced by a method comprising, consisting essentially of, or consisting of, storing said silicone hydrogel in an ozone-free, aqueous solution having a pH of from about 5.0 to less than about 7.2, and a viscosity of less than about 10 centipoise, wherein if the aqueous solution contains a poloxamine or poloxamer surfactant, the surfactant is present in an amount less than about 0.005 weight percent. The terms silicone hydrogel and aqueous solution all have their aforementioned meanings and preferred ranges. "Hydrolytically stable," refers to a lens whose tensile modulus increases less than the tensile modulus of another lens, made of the same material, that has been stored at a pH of more than about 7.3.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

EXAMPLES

The following abbreviations were used in the examples
Lens A=acquafilcon A
Lens B=balafilcon A
DI=deionized water
EDTA =ethylenediaminetetraacetic acid
phosphate-buffered saline, pH 7.4±0.2 PBS;
Phosphate-buffered saline with 0.05% Tween 80, pH 7.4±0.2 TPBS;

Example 1

Measurement of the Mechanical Properties of Lens A at Different pH

Tensile modulus was determined as follows. Twelve lenses were cut into dog-bone shapes and the modulus and elongation to break were measured using and INSTRON™ Model 1122 tensile tester. The lenses were hydrated, using their original packing solution, immediately prior to undergoing testing. The tensile modulus of the 12 lenses were averaged to obtain the mean modulus for the set. Lens A had a modulus of 85.6±10.3 psi when tested prior to conditioning. A saline solution was prepared from 8.48 g/l NaCl, 9.26 g/l boric acid, 1.00 g/l sodium borate and 0.10 g/l EDTA in water. The pH of the solution was adjusted to pH's 6.0, 6.5, 7.0, 7.5 and 8.0 by the addition of small amounts of either 50% NaOH aq. or 37% HCI aq. The lenses were placed in each pH solution and the mixture was heated to 95° C. in sealed vials. The mechanical properties (tensile modulus) of these lenses were measured after one and two weeks at this temperature. The results are shown in Table 1 and FIG. 1.

TABLE 1

| pH | After 1 week @ 95° C. Modulus (psi) | After 2 weeks @ 95° C. Modulus (psi) |
| --- | --- | --- |
| 6.0 | 92.9 ± 4.0 | 104.7 ± 6.3 |
| 6.5 | 89.1 ± 3.3 | 108.8 ± 5.0 |
| 6.8 |  | 126.3 ± 9.9 |
| 7.0 |  | 164.3 ± 16 |
| 7.0 | 109.9 ± 14.8 | 157.8 ± 11.7 |
| 7.2 |  | 236.1 ± 11.8 |
| 7.4 |  | 295.9 ± 28.5 |
| 7.5 | 158 ± 17.7 | 286.8 ± 24.4 |
| 7.6 |  | 338.8 ± 42.6 |
| 8.0 | 294.9 ± 75.2 | 532 ± 76 |

The numerical value of a lens' modulus is inversely proportional to its hydrolytic stability: the lower modulus number, the more stable the lens. These results show that as the pH of the storage solution is lowered, the mechanical stability of the silicone hydrogel increases.

Example 2

Measurement of the Mechanical Properties of Lens B at Different pH

The mechanical properties of Lens B was measured. Lens B has a modulus of 155 (20) psi when tested prior to conditioning. Lenses were placed into saline solution made as in Example 1 at pH's 6.0, 7.0 and 8.0 and heated to 95° C. in sealed vials. The mechanical properties of these lenses were measured after one week at this temperature.

TABLE 2

| pH | After 1 week @ 95° C. Modulus (psi) |
| --- | --- |
| 6.0 | 544 ± 45 |
| 7.0 | 576 ± 21 |
| 8.0 | 1217 ± 102 |

Example 3

Vifilcon (a silicone-free copolymer of 2-hydroxyethyl methacrylate, methacrylic acid, N-vinylpyrrolidone and ethyleneglycol dimethacrylate) soft contact lenses, with an initial modulus of 73.1±7.2 psi, were placed into saline solution made as in Example 1 at pH's 6.0, 7.0 and 8.0 and heated to 95° C. in sealed vials. The mechanical properties of these lenses were measured after two weeks at this temperature. The results, in Table 3, show that unlike those of silicone hydrogels, the moduli of non-silicone hydrogels change very little in accelerated aging tests, and in fact may actually decrease slightly at higher pH.

TABLE 3

| pH | After 2 weeks @ 95° C. Modulus (psi) |
| --- | --- |
| 6.0 | 75.7 ± 4.6 |
| 7.0 | 68.2 ± 5.9 |
| 8.0 | 64.9 ± 4.4 |

What is claimed is:

1. A method comprising stabilizing a silicone hydrogel article against hydrolytic degradation by, storing said silicone hydrogel in an ozone-free, aqueous solution having a pH of from about 5.0 to less than about 7.2, and a viscosity of less than about 10 centipoise, wherein the aqueous solution optionally contains a poloxamine or poloxamer surfactant, in an amount less than about 0.005 weight percent.

2. The method of claim 1 wherein the aqueous solution is saline solution comprising salts selected from one or more members of the group consisting of sodium chloride, boric acid, sodium borate, sodium phosphate, sodium hydrogenphosphate, sodium dihydrogenphosphate, or the corresponding potassium salts of the same.

3. The method of claim 2 wherein the concentration of salt is about 0.3 to 3.0 weight percent.

4. The method of claim 1 wherein the pH of the aqueous solution is about 6.8 to about 7.2.

5. The method of claim 1 wherein the silicone hydrogel article comprises a contact lens.

6. The method of claim 5 wherein the contact lens comprises at least one of acquafilcon A, balafilcon A, or lotrafilcon.

7. The method of claim 1 wherein the viscosity is less than about 7 cps.

8. An article comprising a silicone hydrogel contact lens stabilized against hydrolytic degradation by the step comprising storing said silicone hydrogel in an ozone-free, aqueous solution having a pH of from about 5.0 to less than about 7.2, and a viscosity of less than about 10 centipoise, wherein the aqueous solution optionally contains a poloxamine or poloxamer surfactant, in an amount less than about 0.005 weight percent.

9. The article of claim 8 wherein the pH of the aqueous solution is about 6.8 to about 7.1.

10. The article of claim 8 wherein said contact lens further comprises at least one of acquafilcon A, balafilcon A and lotrafilcon.

\* \* \* \* \*